United States Patent [19]

Kortright et al.

[11] Patent Number: 5,223,398
[45] Date of Patent: Jun. 29, 1993

[54] METHOD FOR SCREENING CELLS OR FORMED BODIES FOR ENUMERATION OF POPULATIONS EXPRESSING SELECTED CHARACTERISTICS

[75] Inventors: Kenneth H. Kortright, Cooper City; Wallace H. Coulter, Miami Springs; Carlos Rodriguez; Thomas Russell, both of Miami; Ronald Paul, North Miami Beach, all of Fla.

[73] Assignee: Coulter Corporation, Hialeah, Fla.

[21] Appl. No.: 587,646

[22] Filed: Sep. 20, 1990

Related U.S. Application Data

[63] Continuation of Ser. No. 025,345, Mar. 13, 1987, abandoned.

[51] Int. Cl.⁵ ............................................. C12Q 1/02
[52] U.S. Cl. ............................ 435/7.24; 435/7.25; 435/29; 435/30; 435/34; 435/39; 436/536; 436/63
[58] Field of Search ............... 435/29, 30, 34, 39, 435/7.24, 7.25

[56] References Cited

U.S. PATENT DOCUMENTS

| | | | |
|---|---|---|---|
| 3,925,018 | 12/1975 | Saunders | 23/230 R |
| 3,970,518 | 7/1976 | Giaever | 195/1.5 |
| 4,141,687 | 2/1979 | Forrest et al. | 23/230 R |
| 4,219,335 | 8/1980 | Ebersole | 436/808 X |
| 4,219,411 | 8/1980 | Yen et al. | 209/213 |
| 4,284,412 | 8/1981 | Hansen et al. | 23/230 B |
| 4,335,094 | 6/1982 | Mosbach | 424/1 |
| 4,452,773 | 6/1984 | Molday | 424/1.1 |
| 4,487,700 | 12/1984 | Kanter | 210/789 |
| 4,499,052 | 2/1985 | Fulwyler | 422/52 |
| 4,581,334 | 4/1986 | Kirchanski et al. | 250/461.2 X |
| 4,599,307 | 7/1986 | Saunders et al. | 435/34 |
| 4,727,020 | 2/1988 | Recktenwald | 356/39 X |
| 4,747,685 | 5/1988 | Suzuki | 356/38 |

OTHER PUBLICATIONS

Leif et al., Clinical Chemistry, vol. 23, (1977) paper 1492-1498.
Owen, Cell Biophysics, vol. 8, 1986, pp. 287-296.
Molday, et al., Federation of European Biochemical Societies Letters, vol. 170, No. 2, May 1984, pp. 232-238.
Molday, et al., Journal of Immunological Methods, 52, 1982, pp. 353-367.
Alpert, Clinical Instrument Systems, vol. 7, No. 5, May 1986, pp. 1-8.

Primary Examiner—Sam Rosen
Attorney, Agent, or Firm—John T. Winburn

[57] ABSTRACT

A method and apparatus for automatically and rapidly, retrieving, counting and/or analyzing at least one selected white blood cell population and/or subset thereof of a whole blood sample or portion thereof. A volume of a biological sample containing the white blood cells is prepared and at least one reactant specific or preferential at least to some selected biological cells is introduced thereto and rapidly mixed for a short period of time. The opacity and/or volume parameter of the cells can be modified and the mixture is then counted and analyzed in one or more steps to obtain the desired white blood cell population analysis.

The biological sample can be a whole blood sample and the reactant can include or be a lyse or a monoclonal antibody bound to microspheres, which will bind to specific ones of the cells or a combination of lyse and microspheres with antibody bound thereto. The microspheres can be magnetic and the bound cells can be magnetically removed for retrieving and analyzing the remaining blood cell population.

52 Claims, 7 Drawing Sheets

METHOD FOR SCREENING CELLS OR FORMED BODIES FOR ENUMERATION OF POPULATIONS EXPRESSING SELECTED CHARACTERISTICS

This is a continuation of copending application Ser. No. 07/025,345 filed on Mar. 13, 1987, now abandoned.

BACKGROUND OF THE INVENTION

This invention relates generally to an automated analyzer and methods of using same for screening biological cells or formed bodies for the enumeration of populations which express selected characteristics for research, diagnostic, medical or industrial purposes. More particularly, the automated analyzers and methods embodying the invention enable multiple part classifications of cells and formed bodies, functional phenotyping of cells and formed bodies, typing of leukemic, lymphoma and solid tumor cells, among others, using a unique combination of electronic technology and the specificity of selective biological molecules, such as antibodies, for such screening and selective enumeration of the cells and formed bodies.

Automation of routine complete blood cell (CBC) analysis of human peripheral blood by an automated blood cell counter was successfully achieved by the COULTER COUNTER ® Model A of Coulter Electronics, Inc. of Hialeah, Fla. The electronic particle sensing system principle of that instrument is disclosed in U.S. Pat. No. 2,656,508 issued Oct. 20, 1953 to Wallace H. Coulter. The use of optical sensing means or lasers, which can be troublesome and expensive. are avoided by particle analyzing instrumentation solely operated on this Coulter electronic sensing principle.

This Coulter sensing principle was developed and expanded into more sophisticated instrumentation such as the COULTER COUNTER ® Model S types of instruments which enabled CBC parameters, absolute cell counts, platelet count and morphology, red blood cell (RBC) morphology, interpretation of normal and abnormal blood specimens by special computer programs.

The Coulter electronic particle sensing principle employs an aperture sensing circuit using a direct current (DC) aperture supply. Such particle sensors are simple in structure, extremely rugged and reliable as attested to by the substantially universal acceptance of the COULTER COUNTER ® automated analyzer in clinical laboratories in the United States and throughout the rest of the World. An improvement in this basic aperture sensing circuit was disclosed in U.S. Pat. No. 3,502,974 issued in 1970 to Wallace Coulter and Walter Hogg. In addition to the standard direct current aperture supply, a high frequency aperture current was applied which enabled the sensing of an additional parameter for classification purposes. The high frequency aperture current produced a signal which is the function of the blood cell's internal conductivity as well as its volume. The signal produced simultaneously by the direct current aperture circuit is a conventional DC amplitude signal which provides an indication primarily of cell volume. The radio frequency amplitude is divided by the direct current pulse amplitude employing a high speed divider circuit to obtain a quotient which is a function of cell volume and internal resistance, conveniently referred to as "opacity". This principle is further described in U.S. Pat. No. 3,502,973 also issued to Wallace Coulter and Walter Hogg in 1970. This parameter has applicability in cell classification systems. Either a single or a pair of separate apertures could be utilized for this purpose.

Classification of different populations is accomplished by collating the data of the signal pairs as they are produced; one, a measure of particle volume and the other a measure of cell internal resistivity or opacity. A convenient form of presenting this data is by two-dimensional plots referred to as scatterplots or scattergrams. Such plots are well described in *Flow Cytometry and Sorting*, page 371; edited by Melamed Melaney, and Mendelsohn, 1979, John Wiley & Sons, NY, N.Y.

FIG. 5A is one example of a data plot of a sample of normal blood. Each dot represents an individual cell. The height above the baseline represents the relative volume of the cell. The distance of the dot to the right of the vertical baseline represents the relative opacity. A plot of normal white blood cells (WBC) (with the red blood cells removed) shows three clusters of dots representing three distinct populations which are a consequence of their intrinsic differences in size and internal composition. If desired, with suitable circuitry, these populations can be enumerated to obtain the numbers of each. The cells are classified on the basis of these inherent differences.

Initial applications of the Coulter electronic particle sensing principle was to perform red blood cell counts and then, more sophisticated determinations of other red blood cell parameters. By removing red blood cells from whole peripheral blood, analysis of the white blood cell populations could be undertaken so long as the red blood cell removal did not significantly impair properties of the remaining white blood cell populations sought to be measured. Red blood cell lysing reagents were developed for this purpose which, though useful and widely applied, were not entirely satisfactory in all respects for subsequent white blood cell determinations.

Previous methods of flow analysis of leukocytes using DC volume alone or light scatter at various angles have shown three clusters of leukocytes corresponding to lymphocytes, monocytes and granulocytes which included the neutrophil, basophil and eosinophil populations. A rough but useful estimation of eosinophil concentration can be made on some samples. The fifth major population is relatively too small for this approach. The eosinophils also have been observed as a distinct cluster using special fluorescence techniques.

These fluorescent techniques were utilized in flow cytometry instruments such as the EPICS ® flow cytometer available from the Coulter Corporation. Such instruments employed the principle of cells moving in a columnar stream bounded by a sheath flow such that cells lined up in single file and passed individually through a laser beam. Light scatter and/or fluorescence signals from the cells were then utilized in classifying cell populations. Staining cells with absorptive or fluorescent dyes made additional cell population classifications possible. The development of instrumentation and fluorochromes for automated multiparameter analysis is further described by R.C. Leif, et al. in Clinical Chemistry, Vol. 23, pp 1492-98 (1977). These developments expanded the number of simultaneous population classifications of leukocytes to four, namely lymphocytes, monocytes, eosinophils and "granulocytes" (neutrophils and basophils).

A more recent analytical hematology instrument has utilized light scattering techniques together with peroxidase enzyme staining (absorptive dye) of cells to produce a five part leukocyte differential. Moreover, dyes in combination with specific reacting biological molecules, such as monoclonal antibodies, have increased, the number of leukocyte classifications possible to include functional sub-divisions.

The invention herein provides a single automated instrument and methods of using the same which combines the application of electronic sensing aperture principles, the specificity of selective biological molecules for identifying and/or enumerating defined populations of cells or formed bodies and microscopic particle technology. The automated analyzer can be used together with a special lysing reagent and/or antibodies coupled to microscopic microspheres or supports of varying composition.

Selectively attaching microscopic particles makes possible the modification of the parameter(s) responsible for the original location of at least one of the populations. The bulk addition of microscopic particles to selected target populations where this addition affects the measured volume and/or opacity results in shifting the location of the dots representing a population.

Antibodies of known specificity are employed in coating microscopic particles. This coating gives the particle the capacity to selectively attach to certain cells which express the antigen the antibody is specific for. These coated or tagged cells are a combination of particles and cell which behave like a new entity. Their parameters of opacity, volume, or both opacity and volume may be considered to represent the sum of the effects of both the cell and the particles on the signals obtained. If the characteristics of the components are different, the new entity will move to a new position in accordance with the net effect. The new location, in contrast with the former position of the cell alone, should allow a classification of such new entity or group of new entities. If the particles attached to the cells are magnetic, then of course, according to current practice, the new entities can be captured by the use of a magnet. If mixed rapidly, unexpected results including complete capture of a population without adversely affecting the properties of cell under study occur.

Only three distinct populations of cells can be readily identified and enumerated from a blood sample by utilizing their inherent and unique properties of DC volume and opacity parameters heretofore stated. Additional steps, such as improved lysing systems, must be taken to enable the detection and enumeration of more populations. Of course, these additional populations represent subpopulations of the three basic ones referred to as lymphocytes, monocytes and granulocytes. The steps performed in accordance with this invention will demonstrate how subpopulations of these basic three populations are obtained.

Employing such simple aperture sensing techniques in combination with two or more biological particles, one can produce a unique and new position of the dot cluster representing a given population. This selective movement of populations on the dot plot or scattergram is reproducible and can be used to classify a population separate from the basic three populations.

The original and inherent combination of DC volume and opacity sensing techniques can be modified through the attachment of microscopic particles to selected individual cells. The selectivity is given the particles by the nature or specificity of the biological molecules, antibodies among others, employed as the coating on their surfaces. A population of cells alone, having no particles on their surface, may occupy a dot plot position no different from other populations or subpopulations and, henceforth, not be distinguishable from one another. The addition of particles having a selective attraction to a specific population of cells which one seeks to identify, enumerate, and study is possible using this approach. The selective addition of a sufficient mass of selective particles to a distinct population of interest results in the shifting of that population's dot plot location as a result of the new and unique combination of mass, volume and opacity.

The separation of specific cell populations is accomplished without materially affecting the properties of remaining cell populations. For example, the removal of erythrocytes or red blood cells (RBC's) from whole blood in accordance with this invention permits the measurement of T4 and/or T8 lymphocytes not otherwise possible with heretofore available chemical RBC lysing reagents. Ratios of the number of T4 versus T8 cells have been used to indicate immune deficiencies consistent with severe viral infections including the AIDS virus among others. The presence of specific receptors on the surface of cells can be used to classify a population into subsets, whose enumeration permits the detection of the onset of disease. For example, in the predominant forms of leukemia there is a sharp rise in peripheral blood lymphocytes. If the subpopulation of lymphocytes which is rapidly proliferating bears the T11 receptor, the patient is at risk of immune abnormalities. Further, if the subpopulation of T11 positive lymphocytes is T4 receptor bearing, then the patient is classified as that common in Japan. Moreover, if the T4 receptor subpopulations expanding is 2H4 positive, then the patient will not only demonstrate a tendency of multiple infections but acute leukemia as well for the T11, T4, 2H4 positive cell is the inducer of suppression and functionally inhibits the patient's ability to make antibodies. Therein, the patient is subject to multiple infections and must be treated for both leukemia and immune deficiency. K. Takatsuki, et al., GANN monograph on Cancer Research 28:13-22, 1982; C. Morimoto, et al., Coulter Japan Symposium, 1984; C. Morimoto, et al., Immunology 134 (3):1508-1515, 1985; C. Morimoto, et al., New England Journal of Medicine 316(2):67-71, 1987. The invention also applies to analyses of formed body suspensions such as bacteria and viruses among others.

This invention provides a single versatile analyzer and methods of using same which combines electronic particle sensing technology and the specificity of selective biological molecules to enable a major advancement in the field of automated analyzers for clinical laboratory use, and for industrial applications. The detection of multiple leukocyte populations, and their relationship to one another in human peripheral blood is important in medical research and the diagnosis of human diseases. Such data are useful as a screening tool for identifying and classifying diseases, such as leukemia. Abnormal situations identified by implementation of the invention herein provides diagnostically relevant information in areas of study not limited only to detection of leukocyte populations as will be apparent from the specification and drawings hereof.

One of the most valuable features of this invention is that it employs the single rugged Coulter sensing operation. It is stable and does not require the complexity and expense of optical systems. The circuitry required for the addition of the RF generator and detector is economical, compact and reliable. A single aperture is all that is required, but the addition of a second or even a third aperture can enable a greater sample throughput rate economically.

SUMMARY OF THE INVENTION

An automated analyzer and method of using same for screening a suspension of biological cells or formed bodies for enumerating populations which express selected characteristics or properties. A sample of cells or formed bodies in suspension is introduced into the analyzer directly. By means of a unique combination of electronic particle sensing aperture technology and the use of the specificity of selective biological molecules alone or coated on the surface of microscopic spheres or supports, as dictated by the expressed properties of the cells or formed bodies in suspension in the sample, multiple part classifications can be achieved.

The analyzer can perform a five part white blood cell differential rapidly yet reliably and simultaneously, can analyze other properties of cells, for instance, utilizing selective antibodies and/or antibodies bound to microspheres of varying composition. The versatility of the automated analyzer enables screening of substantially all biological cells and/or formed bodies directly where biological molecules, such as antibodies for instance, with suitable specificity and binding properties are used for the expressed characteristics of the cells o formed bodies sought to be analyzed.

DESCRIPTION OF THE PREFERRED EMBODIMENTS

Figure 1:
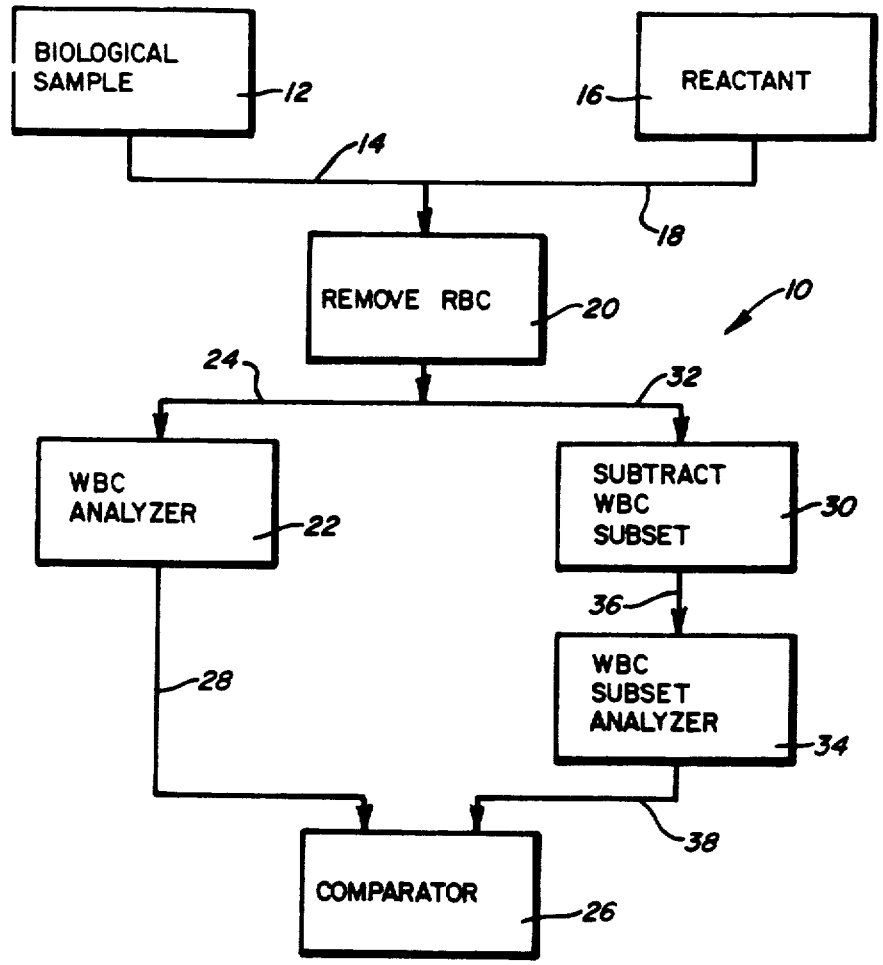
FIG. 1 is a schematic block diagram of one cell population analyzer embodiment of the invention.

Referring to FIG. 1, a first embodiment of a cell population analyzing method and apparatus embodying the present invention is designated generally by the reference numeral 10. The analyzer 10 includes a biological sample 12 which contains at least a first set of viable biological cells (not illustrated), such as in or from a whole blood sample. The cells of the biological sample 12 are to be involved in a biological reaction in a quantitative and/or qualitative determination or analysis. The sample 12 can include a buffer into which the cells are added.

The sample 12 is combined via a line 14 with at least one reactant 16 via a line 18. The red blood cells (RBC) then are removed from the mixture by a functionally designated RBC removing station 20. The RBC's can be removed from the mixture by the station 20 in a number of ways. The RBC's can be lysed by a lyse in the reactant 16. One such preferential lyse and a quench which can be utilized therewith is disclosed in U.S. Ser. No. 025,303, entitled METHOD AND REAGENT SYSTEM FOR ISOLATION, IDENTIFICATION AND-/OR ANALYSIS OF LEUKOCYTES FROM WHOLE BLOOD SAMPLES, filed concurrently herewith, which is incorporated herein by reference. The reactant 16 can be or include a plurality of magnetic microspheres with an antibody specific to the RBC's bound to the microspheres (not illustrated). In this example, the particular red blood cell specific antibody utilized is disclosed in application Ser. No. 799,489, now U.S. Pat. No. 4,752,563, filed Nov. 19, 1985, entitled MONOCLONAL ANTIBODY FOR RECOVERY OF LEUKOCYTES IN HUMAN PERIPHERAL BLOOD AND METHOD OF RECOVERY EMPLOYING SAID MONOCLONAL ANTIBODY, which is incorporated herein by reference. The reactant 16 also can include a buffer in addition to or in place of the sample buffer. The reactant 16 further can be a combination of the preferential RBC lyse and the RBC specific microspheres.

Once the RBC's substantially are removed from the mixture, a portion of the mixture is fed into a white blood cell (WBC) analyzer 22 via a line 24. The WBC analyzer 22 at least counts the number of WBC's in the mixture. The WBC analyzer 22 also can measure one or more volume or opacity parameters of the WBC's. The results from the analyzer 22 are fed to a comparator 26 via a line 28.

A second portion of the RBC deleted mixture is fed to a WBC subset subtracting station 30 via a line 32. The WBC's can be subtracted from the mixture in a number of ways. Microspheres with a monoclonal antibody specific to one of the WBC subsets bound thereto can be added to the mixture. Non-magnetic microspheres can be bound to the WBC's to change or shift the resultant opacity or volume parameters of the cells. Magnetic microspheres also can be bound to the WBC's which then can be removed from the mixture by a magnetic field.

The mixture with the WBC subset population removed or with one or more parameters changed then is fed to a WBC subset analyzer 34 via a line 36. The analyzer 34 can be identical to the analyzer 22. The results of the analyzer 34 then are fed to the comparator 26 via a line 38. The comparator 26 then can compare the WBC results from the analyzer 22 with the modified results from the analyzer 34 to determine at least one characteristic of the selected white blood cell population, such as the number of cells in a particular range.

Figure 2:
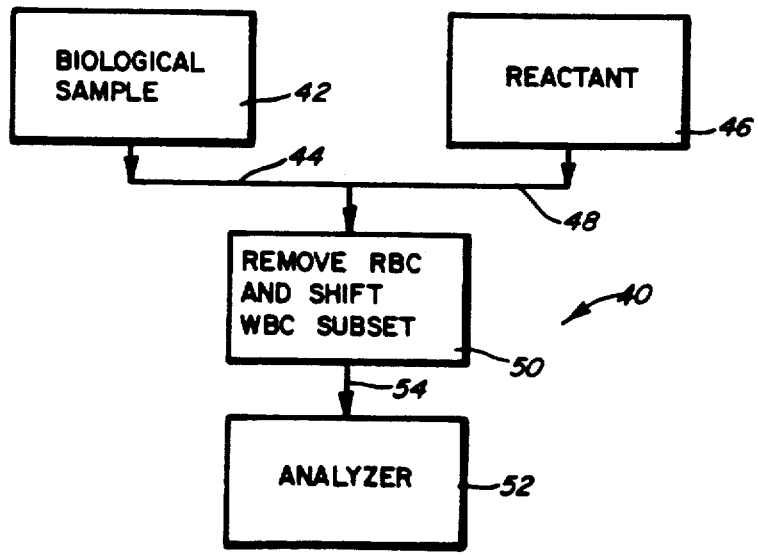
FIG. 2 is a schematic block diagram of a second analyzer embodiment of the invention

Referring to FIG. 2, a second embodiment of a cell population analyzing method and apparatus embodying the present invention is designated generally by the reference numeral 40. The analyzer 40 includes a biological sample 42 which again contains at least a first set of viable biological cells (not illustrated), such as in or from a whole blood sample. The cells of the biological sample 42 are to be involved in a biological reaction in a quantitative and/or qualitative determination or analysis. The sample 42 again can include a buffer into which the cells are added.

The sample 42 is combined via a line 44 with at least one reactant 46 via a line 48. In the analyzer 40, the RBC's are removed from the mixture and simultaneously at least one characteristic of at least one WBC subset is changed or shifted by a functionally designated RBC removing and WBC shifting station 50. As stated above, the RBC's can be removed from the mixture by the station in a number of ways previously enumerated with respect to the station 20. Simultaneously, in the same mixture portion, the WBC's are bound to, generally non-magnetic, microsphere to change or shift the resultant opacity and/or volume parameters of the cells.

The mixture with the RBC's removed and the WBC subset population shifted then is fed to an analyzer 52 via a line 54. The analyzer 52 can be substantially identical to the analyzer 22. The analyzer 40 thus provides a fast, direct analysis of at least one characteristic of a selected WBC population or whole blood subset.

Figure 3:
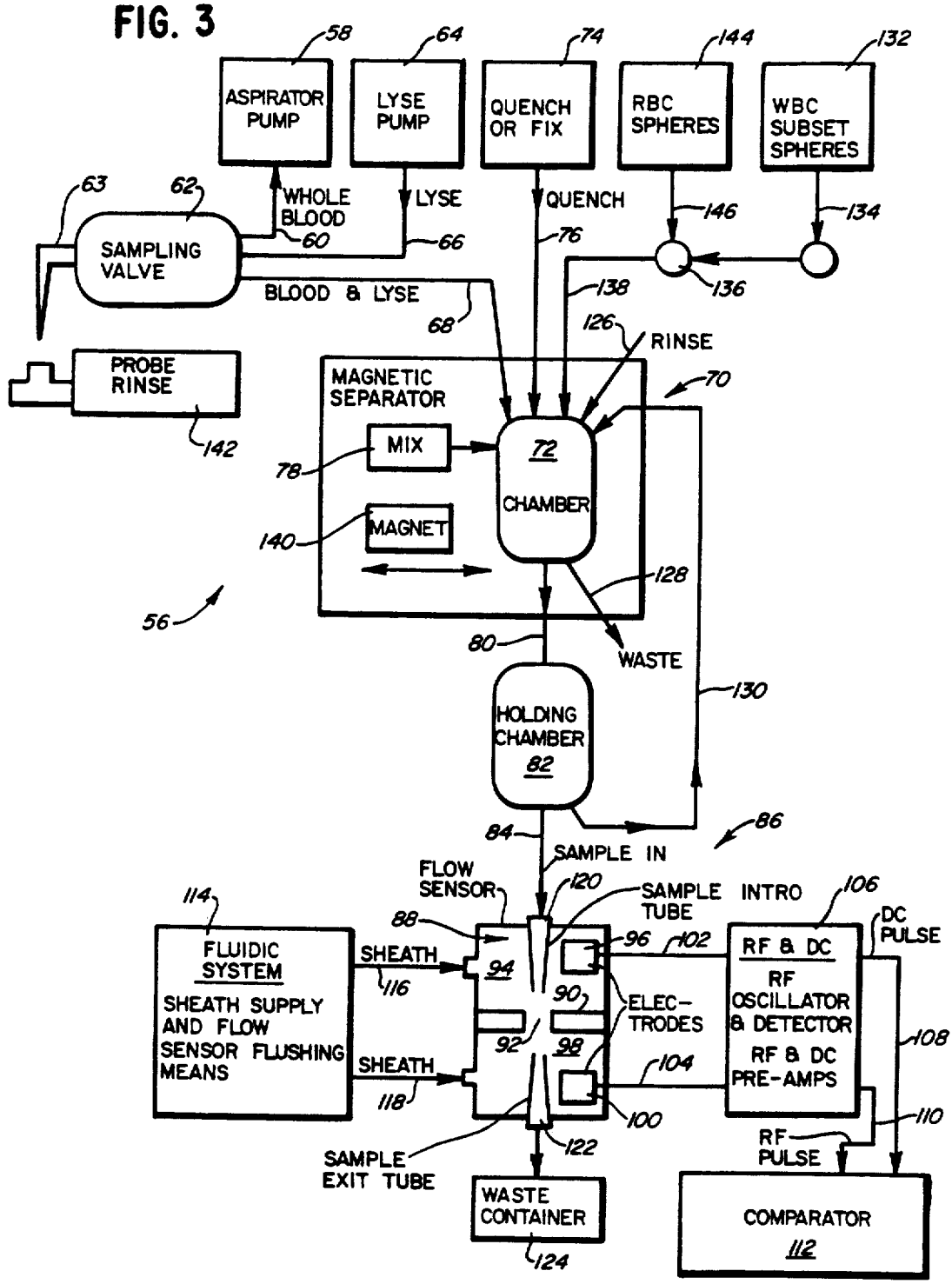
FIG. 3 is one specific analyzer embodiment of the invention corresponding to FIGS. 1 and 2.

One specific embodiment of an analyzer instrument embodying the invention and which can accomplish the analyzing methods of the first and second analyzer 10 and 40, is designated generally by the reference numeral 56 in FIG. 3.

In the instrument 56, only one specific enumeration is illustrated, which can be varied in almost endless detail in accordance with the principles of the invention. Further, the instrument 56 is shown in generally functional detail and the specific embodiments can be structurally implemented in many known ways.

The instrument 56 includes an aspirator pumping mechanism 58 which is utilized to draw the biological sample of interest, for example the sample 12 or 42 into the instrument 56. The aspirator 58 is coupled via a line 60 to a sampling valve 62, which can be coupled to a sample probe 63. A lyse pump 64 can include the lyse, such as part of the reactant 18 or 46 and is also coupled to the valve 62 via a line 66. The valve 62 and the pump 58 can aspirate the biological sample 12 or 42 along with the lyse via the pump 64 when appropriate.

The reactant mixture or the biological sample itself, then is fed via a discharge line 68 into a mixing apparatus 70. The mixer 70 includes a mixing chamber 72 into which the sample or reactant is fed. At this point the operation of the analyzer 10 and 40 differ and hence will be described separately.

In the case of the analyzer 10, if the RBC's have been lysed by the lyse from the pump 64, then when the reaction is completed a quench or fix is supplied from a station 74 via a line 76. The reaction is completed. The reaction can be assisted by mixing the lyse and the sample in the chamber 72 as illustrated functionally at 78.

Specific details of an appropriate mixing apparatus 70, which can be utilized herein are disclosed in U.S. Ser. No. 025,337, entitled METHOD AND APPARATUS FOR RAPID MIXING OF SMALL VOLUMES FOR ENHANCING BIOLOGICAL REACTIONS, filed concurrently herewith, which is incorporated herein by reference. By utilizing the mixer 70 the reactions are greatly enhanced in speed without significantly damaging the properties of interest of the cells, such as, can occur by raising the reaction temperature. Further, the reactions generally are completed in significantly less than a minute, generally on the order of fifteen seconds or less. This allows a rapid analysis of the automatic high volume analyzer instrument 56.

The quenched reactant with the RBC's removed by the lyse (as from the station 20) then is fed via a line 80 to a holding chamber 82, which in this case will hold a second portion of the mixture. A first portion of the mixture will be fed from the chamber 82 via a line 84 to a WBC analyzer 86 (i.e. analyzer 22). The analyzer 86 can be of many physical types in accordance with the counting and sizing techniques described by Wallace H. Coulter in U.S. Pat. No. 2,656,508 and embodied in the numerous commercial blood cell counter of the assignee, Coulter Electronics, Inc.

The analyzer 86, in general, includes a flow sensor or sensing chamber 88. The chamber 88 includes a transducer 90 which has an aperture 92 therethrough. The chamber 88 includes a first portion 99 which has a first electrode 96 in contact with the fluid therein.

The chamber portion 94 and the electrode 96 communicate through the aperture 92 with a second chamber portion 98 having a second electrode 100 therein.

The electrodes 96 and 100 are coupled via reactive leads 102 and 104 to an RF/DC source and sensing circuit 106. The circuit 106 couples both a DC, or low frequency current or signal and a high frequency signal between the electrodes 96 and 100.

The low frequency signal is utilized to sense the amplitude of a signal pulse caused by a cell passing through the aperture 92. The high frequency signal is utilized to obtain the electrical opacity of the same cell passing through the aperture 92.

The measuring of the electrical opacity of cells was described by Wallace H. Coulter and Walter R. Hogg in U.S. Pat. No. 3,502,974 and several patents and publications of the assignee, Coulter Electronics, Inc., since that patent. One specific circuit which can be utilized herein is disclosed in Case 168,008, entitled PARTICLE ANALYZER FOR MEASURING THE RESISTANCE AND REACTANCE OF A PARTICLE, filed Oct. 21, 1986, now U.S. Ser. No. 921,654 which is incorporated herein by reference.

The signals generated by the circuit 106 from the sensed cells are coupled via a DC signal lead 108 and an RF signal lead 110 to a comparator 112 (like the comparator 26). The comparator 112 can hold the signal generated from the first portion, i.e. those without the WBC subset subtracted, for a comparison with the results from the second portion to be described.

The analyzer 86 can include a sheath flow to focus the cells in the sensor 88, in the well known manner. The sheath flow can be provided by a fluidic system 114, coupled to the sensor 88 by a pair of lines 116 and 118 in a known manner. The sample reaction mixture can be fed into the sensor 88 via an introduction tube 120 and can be fed from the sensor 88 via an exit tube 122 into a waste container 124.

While the first portion of the mixture was being analyzed in the analyzer 86, the second portion is held in the chamber 82, while the mixer 72 is cleaned or flushed via a rinse line 126 and exhausted through a waste line 128. Once the chamber 72 is cleansed, the second portion is fed back into the chamber 72 via a line 130. Like the station 30, the WBC subset now is subtracted by adding the WBC microspheres from a station 132 via a line 134, a valve 136 and a chamber line 138.

The WBC microspheres are mixed with the second portion by the mixing mechanism 78. If the WBC microspheres are non-magnetic, the reaction mixture with the bound WBC microspheres is fed via the line 80, the chamber 82 and the line 84 into the analyzer 86, (i.e. the analyzer S4), wherein the second portion is analyzed like the first portion and the results then are compared in the comparator 112 (i.e. the comparator 26). At least one of the WBC subset cell parameters is changed in the second portion, such as the cell opacity by the WBC subset bound microspheres to provide the changed results which then can be analyzed.

If the WBC microspheres are magnetic, then the WBC subset bound thereto are removed by a magnetic field during and/or after the mixing process by a magnetic field or magnet 140. The field can be provided by electromagnetic means or by the magnet 140 being physically moved with respect to the chamber 72 to capture the magnetically bound WBC subset. The second portion without the bound WBC subset then is fed via the line 80, the chamber 82 and line 84 to the analyzer 86 in the manner previously described to obtain the analysis (like the analyzer 34).

The instrument 56 then is prepared to take the next sample for the next analysis. The probe 63 can be cleansed by a probe rinse mechanism 142 and the lines and chambers 72 and 82 can be flushed in a conventional manner. Each analysis of the succeeding sample mixture is obtained in a rapid and automatic fashion. The period between the analysis of succeeding sample mixtures can be on the order of minutes or less.

In operating the analyzer instrument 56, like the analyzer 40, the reaction mixture with the RBC lyse/reactant 46 and the sample 42 is mixed in the chamber 72 along with non-magnetic WBC microspheres from the station 132, which bind to one of the WBC subsets. The quench 74 is added to the reactive mixture which then is fed via the line 80, the chamber 82 and the line 84 to the WBC analyzer 86 for analysis (i.e. like the analyzer 52).

Alternatively to the utilization of the lyse, in either of the analyzers 10 and 40, the sample 12 or 42 can be fed to the mixer 70 via the valve 62 without any lyse. In this case the RBC's can be removed magnetically by utilizing the microspheres with the RBC specific antibody bound thereto from an RBC microsphere station 144 and fed to the valve 136 via a line 146 and hence to the chamber 70 via the line 138. Where no lyse is utilized, the bound RBC's are magnetically removed by the magnet 140 after mixing in a manner substantially identical to the magnetically bound WBC's described above.

Further, in a second case to promote the speed of the reaction, a reaction mixture of the sample with both the RBC lyse and with the RBC magnetic beads can be utilized. The reaction mixture is mixed, the lyse is quenched and the bound RBC's are magnetically removed and then the WBC's are analyzed as previously described.

Figure 4:
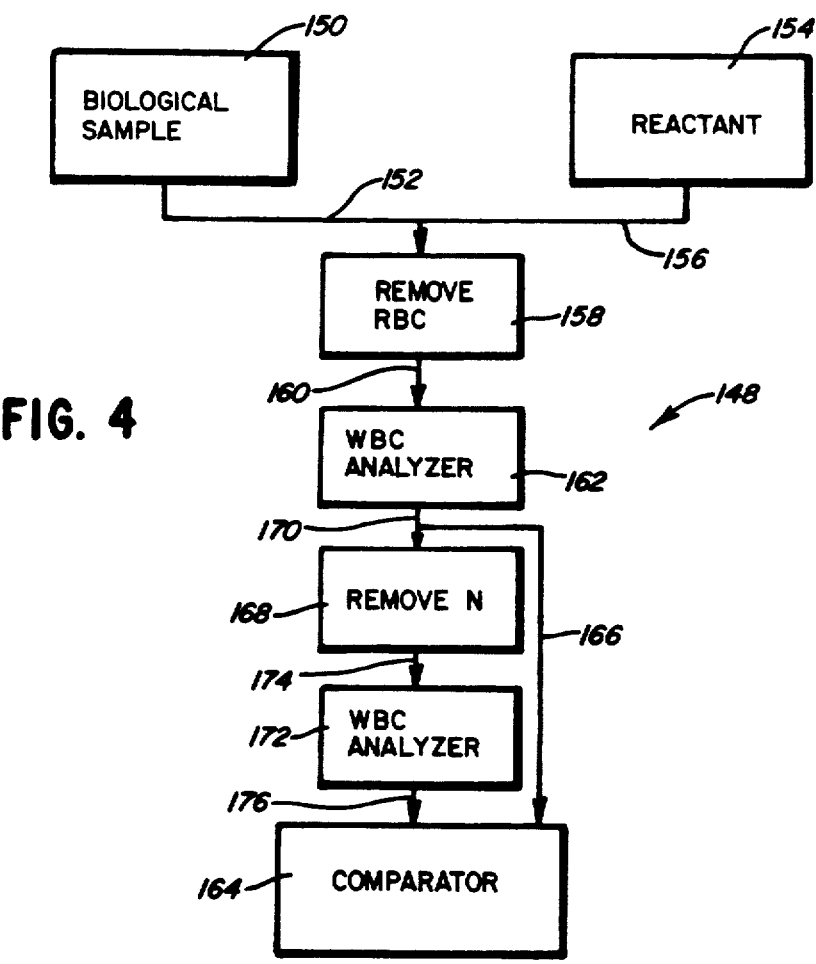
FIG. 4 is a schematic block diagram of another analyzer embodiment of the invention.

Referring now to FIG. 4, another embodiment of a cell population analyzing method and apparatus embodying the present invention is designated generally by the reference numeral 148. The analyzer 148 includes a biological sample 150 which again contains at least a first set of viable biological cells, such as in or from a whole blood sample. The sample 150 again can include a buffer into which the cells are added.

The sample 150 is combined via a line 152 with at least one reactant 154 via a line 156. The RBC's then are removed as above described by a functionally designated RBC removing station 158. The reaction mixture with the RBC's removed is fed via a line 160 into a WBC analyzer 162. The results from the analyzer 162 are fed to a comparator 164 via a line 166, providing a three-part WBC differential with results for monocytes (M), lymphocytes (L) and granulocytes (G).

The mixture then is fed to a neutrophil (N) functionally designated removal station 168 via a line 170. The N's can be removed from the mixture by shifting or changing one parameter, such as opacity, or by magnetic removal, both as described above. In this example, the particular N specific antibody utilized is disclosed in U.S. Ser. No. 938,864, entitled MONOCLONAL ANTIBODY SPECIFIC TO NEUTROPHILS, filed Dec. 8, 1986, now U.S Ser. No. 938,864.

The mixture with the N's removed or shifted then is fed to another WBC analyzer 172 via a line 174. The results of the analyzer 172 are fed to the comparator 164 via a line 176. The results of the analyzer 172 are utilized to obtain a four-part WBC differential with results again for M's and L's, but now in addition since the N's are shifted or removed results for eosinophils (E) and basophils (B) are obtained. The two analytical results from the analyzers 162 and 172 then can be compared by the comparator 164 to form a five-part WBC differential. Specifically, subtracting the number of B's and E's from the number of Gr's results in the number of the removed N's.

Figure 5A:
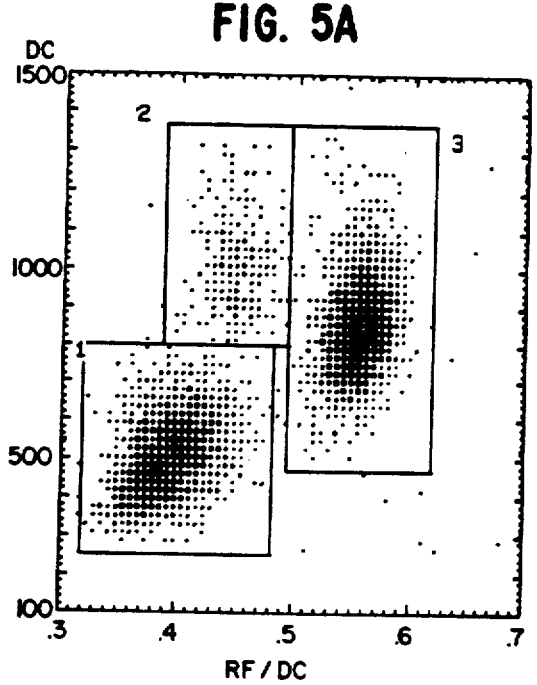
FIGS. 5A and 5B are a scattergram of one set of results utilizing a prototype analyzer system similar to that illustrated with respect to FIGS. 3 and 4.
Figure 5B:
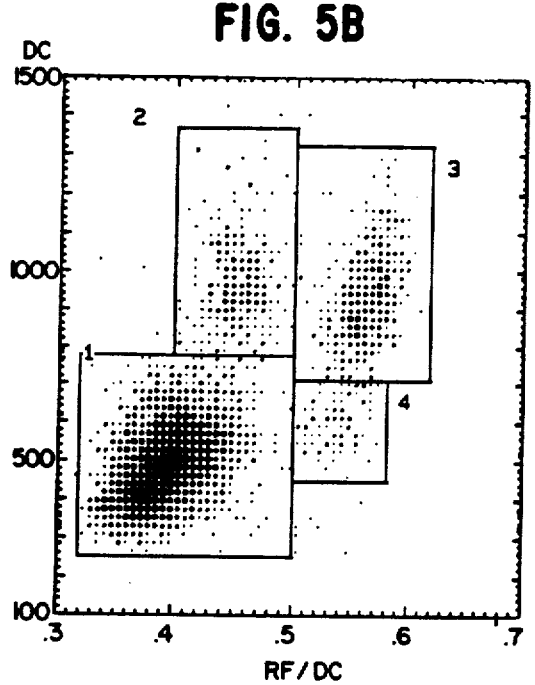

Referring now to FIGS. 5A and 5B, two sets of scattergram results are illustrated obtained from a whole blood sample utilizing a prototype analyzing method similar to the analyzer 148. The biological sample 150 was a 20 microliter sample of whole blood, which was combined with 40 microliters of the magnetic microspheres with the RBC specific antibody bound thereto combined with 140 microliters of buffer solution to form the reactant 154. The reaction mixture was mixed for 15 seconds and placed in a magnetic field for 10 seconds in the station 158. The mixture with the RBC's removed was analyzed by the analyzer 162 as illustrated in the scattergram of FIG. 5A resulting in counts of L's of 45.6 (1), M's of 5.6 (2) and Gr's of 48.7 (3).

The mixture then is combined in the station 168 with 10 microliters of magnetic microspheres with the N specific antibody bound thereto. The mixture is mixed 30 seconds and then placed in a magnetic field for 10 seconds. The mixture with the N's then removed was fed to the analyzer 176 which resulted in the scattergram of FIG. 5B resulting in counts of L's of 81.0 (1), M's of 0.6 (2), E's of 11.0 (3) and B's of 1.8 (4). The comparator 164 then provides the five-part WBC differential of counts of 45.6 L's, 5.6 M's, 41.6 N's, 6.0 E's and 1.2 B's. This corresponds to a standard microscopic five-part WBC differential utilizing Wright stain on the sample on a slide resulting in counts of 44.0 L's, 3.4 M's, 45.0 N's, 6.1 E's and 0.4 B's.

Figure 6:
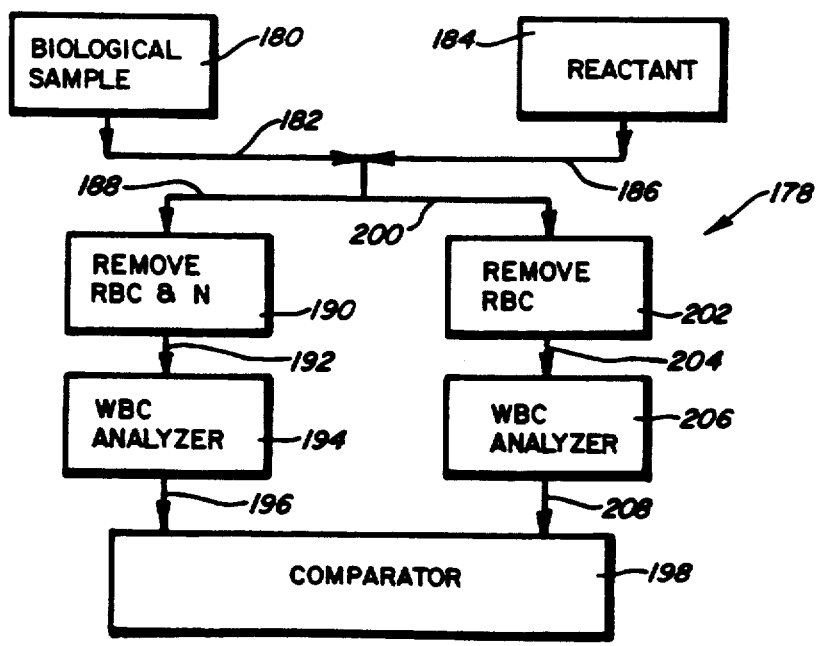
FIG. 6 is a schematic block diagram of a further analyzer embodiment of the invention.

FIG. 6 illustrates a further embodiment of a cell population analyzing method and apparatus embodying the present invention, designated generally by the reference numeral 178. The analyzer 178 includes a biological sample 180 which again contains at least a first set of viable biological cells and also can include a buffer.

The sample 180 is combined via a line 182 with a reactant 184 via a line 186. Functionally illustrated, a first portion of the mixture is fed via a line 188 to a functionally designated RBC and N removing station 190. The RBC's and N's are removed or shifted as described before and the first portion is fed via a line 192 to a WBC analyzer 194.

This provides a result from the analyzer 194 which is fed via a line 196 to a comparator 198. This result includes the above-referenced four-part differential including M's, L's, E's and B's.

At the same time, a second portion of the mixture of the sample 180 and the reactant 184 is fed via a line 200 to a functionally designated RBC removal station 202. The mixture with the RBC's removed is fed via a line 204 to another WBC analyzer 206. The results of the analyzer 206 are fed to the comparator 198 via a line 208. The results of the analyzer 206 directly include the above-referenced three-part WBC differential including M's, L's and Gr's. The results of the analyzers 194 and 206 then are compared by the compartor 198 to provide the five-part WBC differential.

Figure 7:
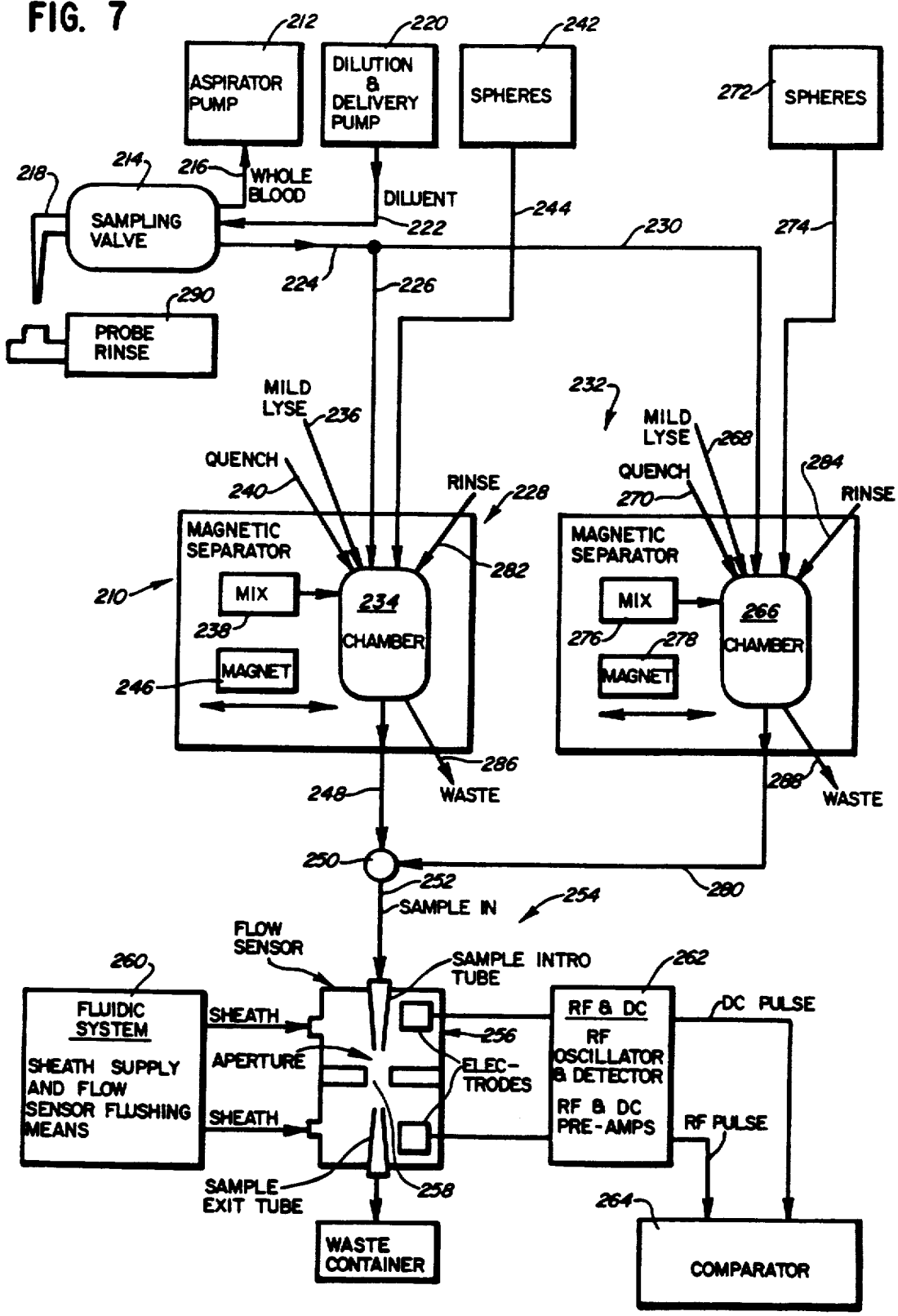
FIG. 7 is a schematic block diagram of a still further analyzer embodiment of the invention.

A specific analyzing instrument embodiment incorporating the method and apparatus of the analyzer 178 is designated generally by the reference numeral 210 in FIG. 7. Again, only one specific hardware enumeration has been illustrated, but like the analyzing instrument 56, the analyzing instrument 210 can be implemented in numerous configurations.

The instrument 210 includes an aspirator purging mechanism 212 which is coupled to a sampling valve 214 via a line 216. The valve 214 can include a sample probe 218 to aspirate the biological sample of interest, such as the sample 180. A diluent delivery pump 220 is coupled to the valve 214 via a line 222 to provide a diluent for the sample, such as a whole blood sample, when desired. A first portion of the mixture then is coupled via a line 224 and a line 226 to a first mixing apparatus 228. At the same time, a second portion of the mixture is fed via the line 224 and a line 230 to a second mixing apparatus 232.

The mixer 228 (comparable to the station 190) is substantially identical to the mixer 232 (comparable to the station 202) and will be described first. The mixer 228 includes a mixing chamber 234 into which the first mixture portion is fed. The mixer 228 includes all of the various options above described and can include a lyse input line 236 for the RBC lyse if desired.

If the lyse is utilized, after mixing as illustrated functionally at 238, then the quench is added via a quench line 240. At the same time, the N's are being removed by the addition of the appropriate magnetic or non-magnetic microspheres with the N specific antibody bound thereto from a source of microspheres 242 fed to the chamber 234 via a line 244. If magnetic microspheres are utilized for the N's or the RBC's, then a magnet 246 or magnetic field is utilized to remove the magnetically bound cells.

The mixed and quenched (where necessary) mixture then is fed via a line 248 through a valve 250 and line 252 to a WBC analyzer 254 (i.e. analyzer 194). The analyzer 254 is the same as the analyzer 86 and will not be described again in such detail. Again, the analyzer 254 includes a sensing chamber 256 with an aperture 258 therein through which the mixture and cells pass. A sheath flow fluidic system 260 can be coupled to the chamber 256. The signals generated by the cells are detected by an RF/DC source and sensing circuit 262 whose outputs are fed to a comparator 264, as previously described.

Concurrently, the second mixture portion is fed into a mixing chamber 266. In the second portion, only the RBC's are removed (i.e. like the station 202) and the RBC's can be removed by the RBC lyse fed into the chamber 266 via a line 268. The lyse is mixed with the sample and then a quench is added via a quench line 270. Alternatively the RBC's can be removed by magnetic microspheres having the RBC specific antibody bound thereto from a microsphere source 272 fed into the chamber 266 via a line 274. The microspheres are fixed, functionally at 276, and then the magnetically bound RBC microspheres are removed by a magnet 278.

The RBC removed mixture then is fed via a line 280 to the valve 250 and via the line 252 to the analyzer 254 to obtain the above-mentioned results. The mixers 228 and 232 include appropriate respective rinse lines 282 and 284 and waste lines 286 and 288 and a probe rinse 290 to cleanse the instrument 210 prior to aspirating the next sample or sample for analyzing.

Figure 8A:
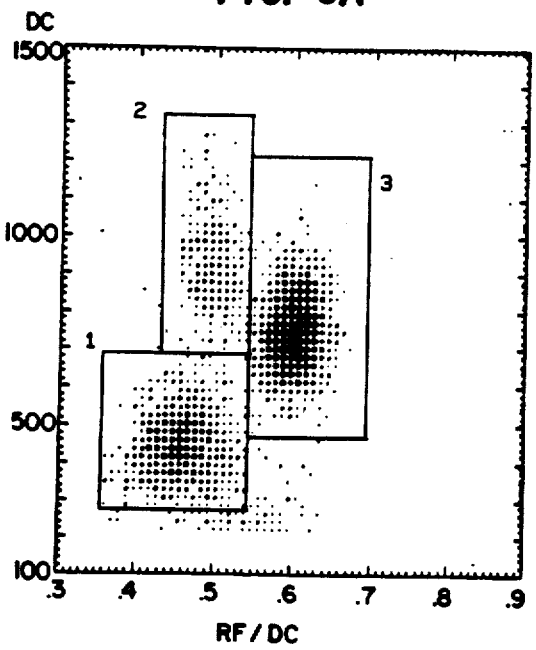
FIGS. 8A and 8B, 9A and 9B, 10A and 10B and 11A and 11B are a scattergram of one set of results utilizing a prototype analyzer system similar to that illustrated with respect to FIGS. 6 and 7.
Figure 8B:
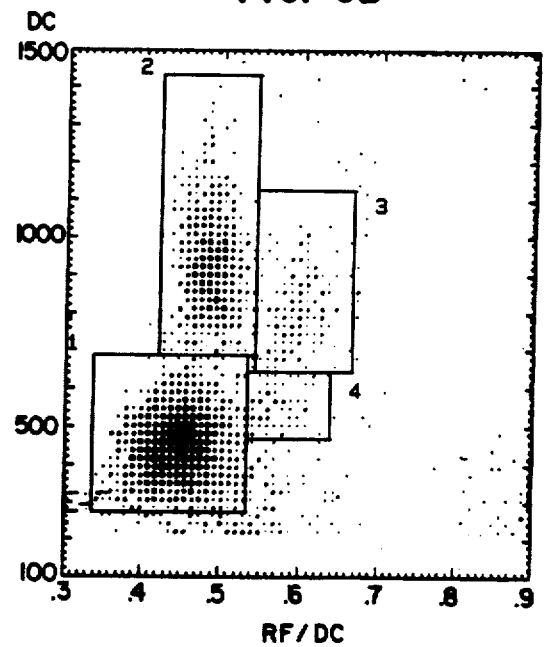

FIGS. 8A and 8B illustrate scattergram results obtained from a whole blood sample utilizing an analyzing method similar to the analyzer 178. In this example, 20 microliters of whole blood form the sample 180, while 40 microliters of magnetic microspheres with the RBC specific antibody bound thereto combined with 140 microliters of buffer solution form the reactant 184. A portion of the mixture is mixed for 20 seconds in the station 202 and then placed in a magnetic field for 10 seconds. The RBC removed mixture then is analyzed in the analyzer 206 resulting in the scattergram of FIG. 8A which provides a count of L's 29.4 (1), M's 8.1 (2) and Gr's 62.4 (3).

At the same time, another portion of the same mixture is combined with 10 microliters of magnetic microspheres with the N specific antibody bound thereto to remove the RBC's and N's in the station 190. The mixture is mixed for 30 seconds, then placed in a magnetic field for 10 seconds. The mixture with the N's and RBC's removed then is analyzed by the analyzer 194 resulting in the scattergram of FIG. 8B which provides a count of L's 73.5 (1), M's 21.7 (2), E's 3.4 (3) and B's 1.4 (4). The two counts are compared in the comparator 198, resulting in a five-part WBC differential count of L's 29.4, M's 8.0, N's 60.8, E's 1.2 and B's 0.6. A microscope comparison again was made resulting in counts of L's 29.4, M's 5.0, N's 65.0, E's 1.0 and B's of less than 1.0.

Figure 9A:
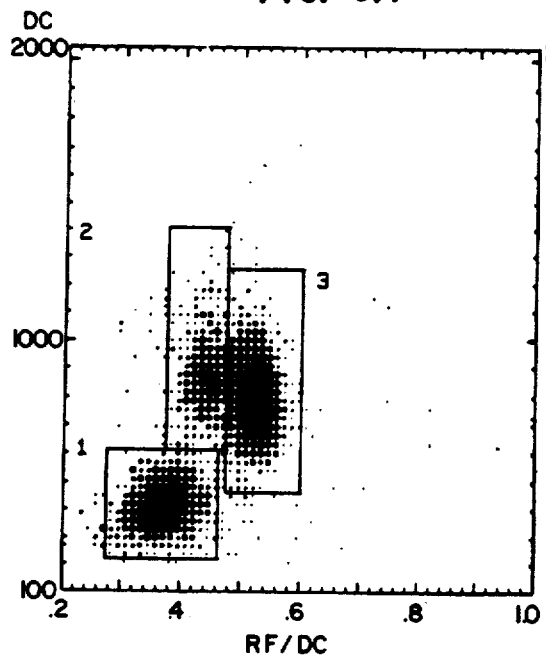
Figure 9B:
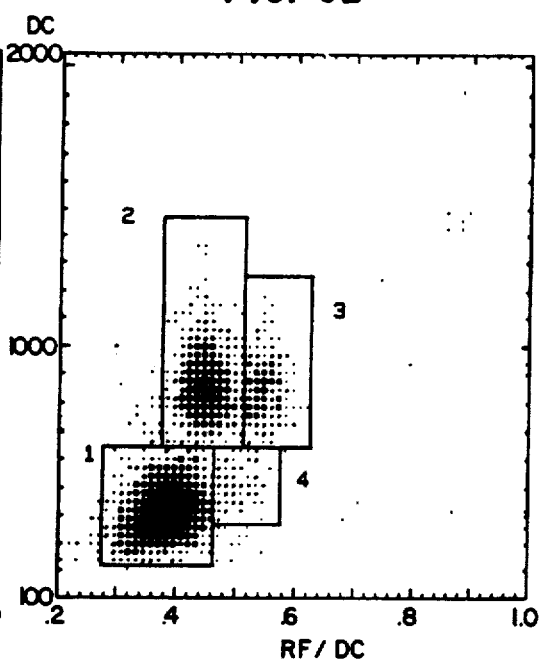

FIGS. 9A and 9B show scattergram results of a five-part WBC differential example similar to that of FIGS. 8A and 8B. A 20 microliter sample of whole blood was analyzed in the same steps described with respect to FIGS. 8A and 8B resulting in the scattergram of FIG. 9A providing a count of L's 35.4 (1), M's 14.6 (2) and Gr's 50.0 (3). The scattergram of FIG. 9B provides a count of L's 66.4 (1), M's 25.0 (2), E's 6.6 (3) and B's 2.0 (4). The resulting five-part WBC differential results in counts of 35.4 L's, 14.6 M's, 45.5 N's, 3.5 E's and 1.1 B's was compared to a microscope count of 36 L's, 11 M's, 49 N's, 3 E's and 1 B.

Figure 10A:
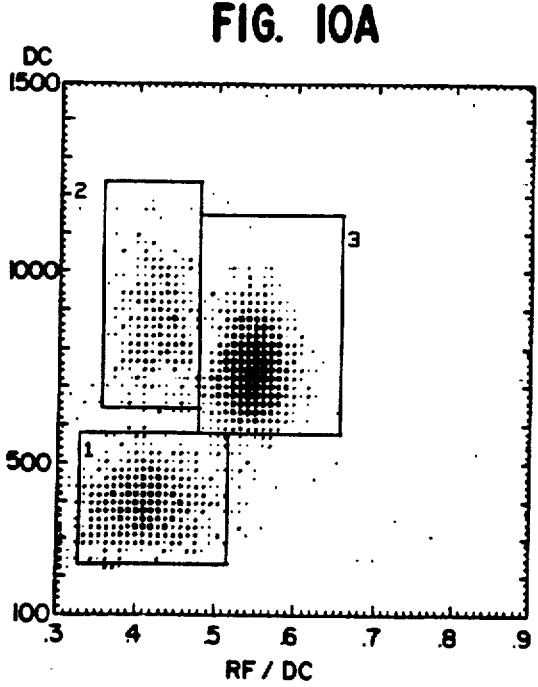
Figure 10B:
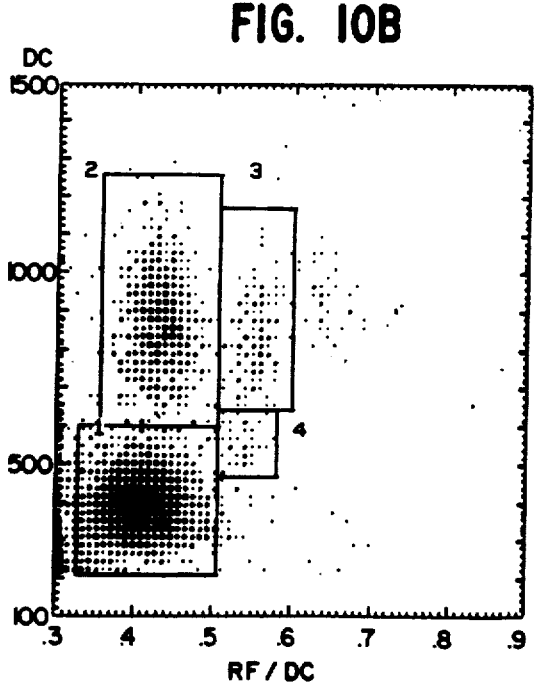

FIGS. 10A and 10B show scattergram results of a five-part WBC differential again similar to that of FIGS. 8A, 8B and 9A, 9B, however, in this example, lyse was utilized. In this example, 20 microliters of whole blood was combined with 80 microliters of buffer and 240 microliters of the RBC preferential lyse above referenced. The mixture is mixed for 6 seconds and then a quench is added. The time period is significant, because the lyse left unquenched for a period of time greater than about 10 seconds will start to affect the significant properties of the WBC's. The mixture with the RBC's removed is analyzed to provide the scattergram of FIG. 10A resulting in counts of L's 25.7 (1), M's 9.6 (2) and Gr's 65.0 (3).

A second portion of the mixture including a second 20 microliter sample of the whole blood is combined with 120 microliters of buffer and 10 microliters of magnetic microspheres with the N specific antibody bound thereto and mixed for 30 seconds and then placed in a magnetic field for 10 seconds. The RBC preferential lyse then is added to the N removed mixture which then is mixed for 6 seconds before it is quenched. The resulting scattergram FIG. 10B results in percentage counts of L's 74.6 (1), M's 21.6 (2), E's 2.9 (3) and B's 0.8 (4). The resulting five-part WBC differential results in percentage counts of L's 25.6, M's 9.6, N's 63.5, E's 1.06 and B's 0.3. Again a microscope comparison resulted in counts of L's 29.4, M's 5.0, N's 65.0, E's 1.0 and B's of less than 1.

Figure 11A:
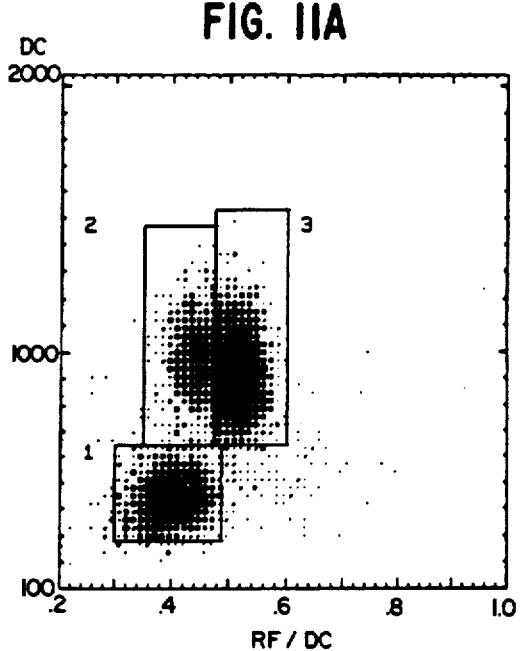
Figure 11B:
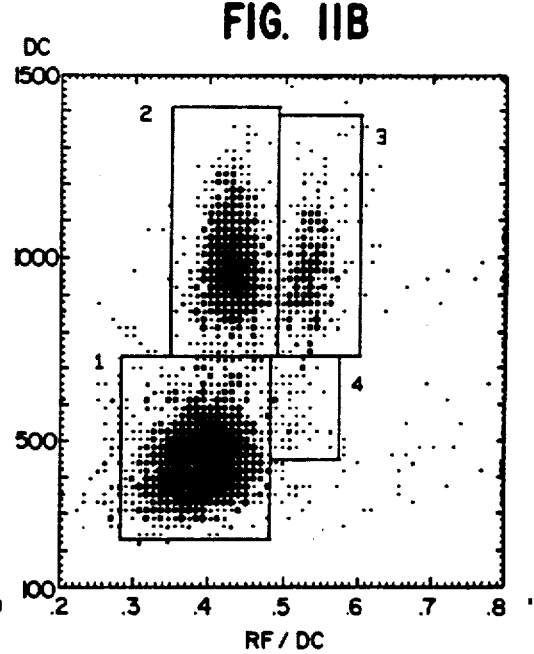

Another example of scattergram results of a five-part WBC differential similar to that of FIGS. 10A and 10B is illustrated in FIGS. 11A and 11B. A sample of whole blood had two samples simultaneously analyzed in the same steps described with a respect to FIGS. 10A and 10B. The scattergram of FIG. 11A provides a count of L's 31.9 (1), M's 17.6 (2) and Gr's 50.4 (3). The scattergram of FIG. 11B provides a count of L's 67.1 (1), M's 24.1 (2), E's 7.6 (3) and B's 1.2 (4). The resulting five-part WBC differential results in counts of 31.9 L's, 11.4 M's, 46.0 N's, 3.6 E's and 0.7 B's as compared to a microscope count of 36 L's, 11 M's, 49 N's, 3 E's and 1 B's.

Figure 12:
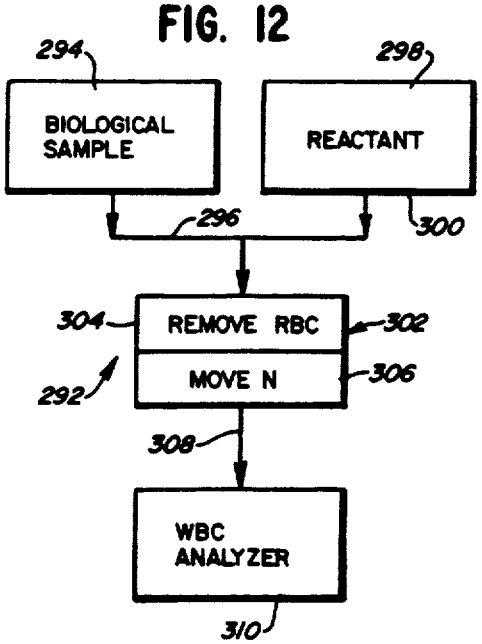
FIG. 12 is a schematic block diagram of a yet still further analyzer embodiment of the invention; an FIG. 13 is a scattergram of one set of results utilizing a prototype analyzer system similar to that illustrated with respect to FIG. 12.

A yet still further embodiment of a cell population analyzing method and apparatus embodying the present invention is designated generally by the reference numeral 292 in FIG. 12. The analyzer 292 includes a biological sample 294, again including at least a first set of viable biological cells and including a buffer if desired.

The sample 294 is combined via a line 296 with at least one reactant 298 via a line 300. In the analyzer 292, the RBC's are removed and the N's are shifted sequentially or simultaneously in a functionally designated station 302. The RBC remove function is designated 304 and the N move or shift portion is designated 306 to indicate that the functions can be performed simultaneously or sequentially. The RBC's can be removed magnetically or with lyse or with a combination of the two as previously described. The N's are removed or shifted by adding microspheres having an N specific antibody bound thereto to the mixture.

Once the RBC's are removed and the N's are moved or shifted, then the resulting mixture is fed via a line 308 to an analyzer 310. In this case, the N's are shifted sufficiently from the patterns of the E's and B's that a five-part WBC differential of M's, L's, E's, B's and N's is directly obtained. The functions of the analyzer 292 can be performed on either of the instruments 56 and 210 or minor variations thereof.

Figure 13:
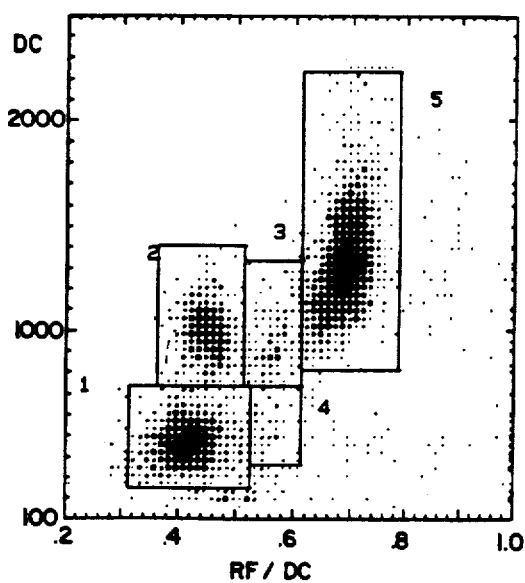

The scattergram results of one example of a direct five-part WBC differential in accordance with the analyzer 292 is illustrated in FIG. 13. In this example, the biological sample 294 is 20 microliters of a whole blood sample and the reactant 298 is 10 microliters of nonmagnetic microspheres with the N specific antibody bound thereto combined with 100 microliters of buffer and mixed in the substation 306 for 30 seconds. The RBC preferential lyse, 10 microliters thereof, then is added to the mixture which is mixed in the substation 304 for 6 seconds after which the quench is added. The RBC removed and N shifted mixture then is analyzed by the analyzer 310 resulting in the scattergram of FIG. 13 which provides a direct count of 29.6 L's, 13.6 M's, 52.2 N's, 3.4 E's and 1.06 B's as compared to a microscope determination of 35 L's, 5 M's, 56 N's, 4 E's and no B's. In this particular example, the whole blood sample was also analyzed on a general cell counting instrument of Coulter Electronics, Inc., which resulted in 29 L's, 11.1 M's and 59.9 Gr's (N's, E's and B's).

Many modifications and variations of the present invention are possible in light of the above teachings. The samples 12, 42, 150, 180 and 294 can include whole blood, human body fluids containing cells, or other fluids containing formed bodies, such as bacteria, viruses and fungi. The volumes of microspheres specified are stated in weight of microspheres per volume of diluent. It is therefore, to be understood that within the scope of the appended claims, the invention may be practiced otherwise than as specifically described.

What is claimed and desired to be secured by Letters Patent of the United States is:

1. A method of obtaining a not otherwise obtainable multi-part white blood cell population differential from a whole blood sample having at least a red blood cell population and white blood cell populations therein for identification and/or enumeration and/or study, comprising:

removing said red blood cell population from said sample without adversely affecting relevant qualities and/or quantities of said white blood cell populations;

electronically sensing and counting at least said white blood cell populations of granulocytes, monocytes and lymphocytes with at least two different electronic parameters to provide a total white blood cell population count;

removing or shifting the neutrophil population contribution from said white blood cell populations by providing microspheres having a neutrophil specific monoclonal antibody bonded thereto and mixing said microspheres with said sample to bind to said neutrophil population and in so doing allowing for the electronic sensing of eosinophils and basophils;

electronically sensing and counting at least said remaining white blood cell populations of monocytes, lymphocytes, eosinophils and basophils with at least two different electronic parameters; and comparing said counts to derive a count of said white blood cell population of neutrophils and thereby obtaining at least a five-part white blood cell differential.

2. The method as defined in claim 1 wherein removal of said red blood cell population includes providing microspheres having a red blood cell specific monoclonal antibody bonded thereto and mixing said microspheres with said whole blood sample to bind to said red blood cell population; and removing said microspheres with said bound red blood cells from said whole blood sample.

3. The method as defined in claim 2 including providing magnetic microspheres and a magnetic field and removing said red blood cells from said whole blood sample by removing the remainder of said whole blood sample while attracting said magnetic microspheres within said magnetic field.

4. The method as defined in claim 2 including mixing said microspheres with said whole blood sample to bind said red blood cell population to said microspheres in less than sixty seconds.

5. The method as defined in claim 1 wherein removing said red blood cell population includes providing microspheres having a red blood cell specific monoclonal antibody bonded thereto and mixing said microspheres with said whole blood sample to bind to said red blood cell population and providing a red blood cell lyse with said microspheres to eliminate a portion of said red blood cell population to decrease the number of microspheres necessary to remove said red blood cell population; and removing said microspheres with said red blood cells bound thereto from said whole blood sample.

6. The method as defined in claim 5 including providing magnetic microspheres and a magnetic field and removing said red blood cells from said whole blood sample by removing the remainder of said whole blood sample while attracting said magnetic microspheres within said magnetic field.

7. The method as defined in claim 5 including mixing said microspheres with said whole blood sample to bind said red blood cell population to said microspheres in less than sixty seconds and to provide said lysing action.

8. The method as defined in claim 1 wherein removing said red blood cell population includes providing a red blood cell lyse to substantially eliminate said red blood cell population.

9. The method as defined in claim 1 including providing microspheres having a neutrophil specific monoclonal antibody bonded thereto and mixing said microspheres with said sample to bind to said neutrophil population to shift at least one sensed electronic characteristic of said neutrophil population.

10. The method as defined in claim 1 including providing microspheres having a neutrophil specific monoclonal antibody bonded thereto and mixing said microspheres with said sample to bind to said neutrophil population; and removing said microspheres with said neutrophil population bound thereto from said sample.

11. The method as defined in claim 10 including providing magnetic microspheres and a magnetic field and removing said neutrophil population from said whole blood sample by removing the remainder of said whole blood sample while attracting said magnetic microspheres within said magnetic field.

12. The method as defined in claim 10 including mixing said microspheres with said sample to bind said neutrophil population to said microspheres in less than sixty seconds.

13. The method as defined in claim 1 including said two electronic parameters being a low frequency and a high frequency signal.

14. A method of obtaining a not otherwise obtainable multi-part white blood cell population differential from a whole blood sample having at least a red blood cell population and white blood cell populations therein for identification and/or enumeration and/or study, comprising:

removing said red blood cell population from a first portion of said sample without adversely affecting the relevant qualities and/or quantities of said white blood cell populations;

electronically sensing and counting at least said white blood cell populations of granulocytes, monocytes and lymphocytes in said first portion with at least two different electronic parameters to provide a total white blood cell population count;

removing said red blood cell population from a second portion of said sample;

removing or shifting the neutrophil population contribution from said white blood cell populations without adversely affecting the relevant qualities and/or quantities of said remaining white blood cell populations by providing microspheres having a neutrophil specific monoclonal antibody bonded thereto and mixing said microspheres with said sample to bind to said neutrophil population and in so doing allowing for the electronic sensing of eosinophils and basophils;

electronically sensing and counting at least said remaining white blood cell populations of monocytes, lymphocytes, eosinophils and basophils in said second portion with at least two different electronic parameters; and comparing said counts from said first and second portions to derive a count of said white blood cell population of neutrophils and thereby obtaining at least a five-part white blood cell differential.

15. The method as defined in claim 14 wherein removing said red blood cell population from at least one of said portions including providing microspheres having a red blood cell specific monoclonal antibody bonded thereto and mixing said microspheres with said whole blood sample to bid to said red blood cell population; and removing said microspheres with said red blood cells bound thereto from said whole blood sample.

16. The method as defined in claim 15 including providing magnetic microspheres and a magnetic field and removing said red blood cells from said whole blood sample by removing the remainder of said whole blood sample while attracting said magnetic microspheres within said magnetic field.

17. The method as defined in claim 15 including mixing said microspheres with said whole blood sample to bind said red blood cell population to said microspheres in less than sixty seconds.

18. The method as defined in claim 14 wherein removing said red blood cell population from at least one of said portions includes providing microspheres having a red blood cell specific monoclonal antibody bonded thereto and mixing said microspheres with said whole blood sample to bind to said red blood cell population and providing a red blood cell lyse with said microspheres to eliminate a portion of said red blood cell population to decrease the number of microspheres necessary to remove said red blood cell population; and removing said microspheres with said red blood cells bound thereto from said whole blood sample.

19. The method as defined in claim 18 including providing magnetic microspheres and a magnetic field and removing said red blood cells from said whole blood sample by removing the remainder of said whole blood sample while attracting said magnetic microspheres within said magnetic field.

20. The method as defined in claim 18 including mixing said microspheres with said whole blood sample portion to bind said red blood cell population to said microspheres in less than sixty seconds and to provide said lysing action.

21. The method as defined in claim 14 wherein removing said red blood cell population from at least one of said portions including providing a red blood cell lyse to substantially eliminate said red blood cell population.

22. The method as defined in claim 14 including providing microspheres having a neutrophil specific monoclonal antibody bonded thereto and mixing said microspheres with said whole blood sample to bind to said neutrophil population to shift at least one electronic characteristic of said neutrophil population.

23. The method as defined in claim 14 including providing microspheres having a neutrophil specific monoclonal antibody bonded thereto and mixing said microspheres with said whole blood sample to bind to said neutrophil population; and
   removing said microspheres with said neutrophil population bound thereto from said sample.

24. The method as defined in claim 23 including providing magnetic microspheres and a magnetic field and removing said neutrophil population from said whole blood sample by removing the remainder of said whole blood sample while attracting said magnetic microspheres within said magnetic field.

25. The method as defined in claim 23 including mixing said microspheres with said whole blood sample to bind said neutrophil population to said microspheres in less than sixty seconds.

26. The method as defined in claim 14 including said two electronic parameters being a low frequency and a high frequency signal.

27. A method of obtaining a not otherwise obtainable multi-part white blood cell population differential from a whole blood sample having at least a red blood cell population and white blood cell populations therein for identification and/or enumeration and/or study, comprising:
   removing said red blood cell population from said sample without adversely affecting relevant qualities and/or quantities of said white blood cell populations;
   shifting the neutrophil population electronic sensing characteristic contribution with respect to the other white blood cell populations by providing microspheres having a neutrophil specific monoclonal antibody bonded thereto and mixing said microspheres with said sample to bind to said neutrophil population to shift at least one electronic characteristic of said neutrophil population, said microspheres being substantially smaller than said cells, and in so doing allowing for the electronic sensing of eosinophils and basophils; and
   electronically sensing and counting at least said white blood cell populations of monocytes, lymphocytes, neutrophils, eosinophils and basophils with at least two different electronic parameters and thereby obtaining at least a five-part white blood cell differential.

28. The method as defined in claim 27 wherein removing said red blood cell population includes providing microspheres having a red blood cell specific monoclonal antibody bonded thereto and mixing said microspheres with said whole blood sample to bind to said red blood cell population; and
   removing said microspheres with said red blood cells bound thereto from said whole blood sample.

29. The method as defined in claim 28 including providing magnetic microspheres and a magnetic field and removing said red blood cells from said whole blood sample by removing the remainder of said whole blood sample while attracting said magnetic microspheres within said magnetic field.

30. The method as defined in claim 28 including mixing said microspheres with said whole blood sample to bind said red blood cell population to said microspheres in less than sixty seconds.

31. The method as defined in claim 27 wherein removing said red blood cell population including providing microspheres having a red blood cell specific monoclonal antibody bonded thereto and mixing said microspheres with said whole blood sample to bind to said red blood cell population and providing a red blood cell lyse with said microspheres to eliminate a portion of said red blood cell population to decrease the number of microspheres necessary to remove said red blood cell population; and
   removing said microspheres with said red blood cells bound thereto from said whole blood sample.

32. The method as defined in claim 31 including providing magnetic microspheres and a magnetic field and removing said red blood cells from said whole blood sample by removing the remainder of said whole blood sample while attracting said magnetic microspheres within said magnetic field.

33. The method as defined in claim 31 including mixing said microspheres with said whole blood sample to bind said red blood cell population to said microspheres in less than sixty seconds and to provide said lysing action.

34. The method as defined in claim 27 wherein removing said red blood cell population includes providing a red blood cell lyse to substantially eliminate said red blood cell population.

35. The method as defined in claim 27 including mixing said microspheres with said sample to bind said neutrophil population to said microspheres in less than sixty seconds.

36. The method as defined in claim 27 including said two electronic parameters being a low frequency and a high frequency signal.

37. A method of obtaining at least one white blood cell population analysis not otherwise obtainable for identification and/or enumeration and/or study from a whole blood sample having at least a red blood cell population and white blood cell populations therein, at least one of said white blood cell populations further having at least two subsets, comprising:
   removing said red blood cell population from said sample without significantly adversely affecting relevant qualities and/or quantities of said white blood cell populations;
   removing or shifting at least one white blood cell population subset contribution from a selected specific white blood cell population by binding microspheres having a monoclonal antibody bonded thereto specific to said white blood cell population subset to said white blood cell population subset; and
   electronically sensing and analyzing said removed or shifted white blood cell population subset and said selected white blood cell population with at least two different electronic parameters to determine at least two characteristic of said selected white blood cell population.

38. The method as defined in claim 37 including said two electronic parameters being a low frequency and a high frequency signal.

39. A method of obtaining at least one white blood cell population or population subset analysis not otherwise obtainable for identification and/or enumeration and/or study from a whole blood sample having at least white blood cell populations therein including at lest one white blood cell population subset, comprising:

electronically sensing and counting with at least two different electronic parameters at least the white blood cell populations and subsets thereof to form a first total count;

removing at least one of the white blood cell populations or a subset thereof by binding microspheres having a monoclonal antibody bonded thereto specific to at least one of said white blood cell populations or subset thereof to at least one of said white blood cell populations or a subset thereof;

electronically sensing and counting with at least two different electronic parameters at least the remaining white blood cell populations without the removed population or subset to form a second count; and comparing said counts to obtain or derive at least one of
(a) the remaining white blood cell populations without the removed population or subset,
(b) the removed white blood cell population or subset population, or
(c) both the remaining and removed white blood cell populations.

40. The method as defined in claim 39 wherein removing at least one of the white blood cell populations or a subset thereof includes providing microspheres having a monoclonal antibody specific to at least one of the white blood cell populations or a subset thereof bonded thereto and mixing said microspheres with said sample to bind to at least one of the white blood cell populations or a subset thereof; and
removing said microspheres with at least one of the white blood cell populations or a subset thereof bound thereto from said sample.

41. The method as defined in claim 40 including providing magnetic microspheres and a magnetic field and removing said at least one of the white blood cell populations or a subset thereof from said sample by removing the remainder of the same while attracting said magnetic microspheres within said magnetic field.

42. The method as defined in claim 39 including removing the neutrophil population.

43. The method as defined in claim 39 including sequentially utilizing one portion of the sample to form said first count, remove said at least one of the white blood cell populations or a subset thereof and form said second count.

44. The method as defined in claim 39 including utilizing a first portion of the sample to form said first count and utilizing a second portion of the sample to remove said at least one of the white blood cell populations or a subset thereof and form said second count.

45. The method as defined in claim 39 including said two electronic parameters being a low frequency and a high frequency signal.

46. A method of obtaining at least one white blood cell population or population subset analysis not otherwise obtainable for identification and/or enumeration and/or study from a whole blood sample having at least white blood cell populations therein including at least one white blood cell population subset, comprising:

electronically sensing and counting at least the white blood cell populations and subsets thereof with at least two different electronic parameters to form a first total count;

shifting at least one of the white blood cell populations or a subset thereof by binding microspheres having a monoclonal antibody bonded thereto specific to at least one of said white blood cell populations or subset thereof to at least one of said white blood cell populations or a subset thereof, said microspheres being substantially smaller than said cells;

electronically sensing and counting with at least two different electronic parameters at least one of
(a) the remaining white blood cell populations without the shifted population or subset,
(b) the shifted white blood cell population or subset population, or
(c) both the remaining and shifted white blood cell populations; and comparing said counts to obtain or derive at least one of
(a) the remaining white blood cell populations without the shifted population or subset,
(b) the shifted white blood cell population or subset population, or
(c) both the remaining and shifted white blood cell populations.

47. The method as defined in claim 46 wherein shifting at least one of the white blood cell populations or a subset thereof includes providing microspheres having a monoclonal antibody specific to at least one of the white blood cell populations or a subset thereof to shift at least one sensed electronic characteristic of said at least one of the white blood cell populations or a subset thereof.

48. The method as defined in claim 46 including shifting the neutrophil population.

49. The method as defined in claim 46 including sequentially utilizing one portion of the sample to form said first count, shift said at least one of the white blood cell populations or a subset thereof and form said second count.

50. The method as defined in claim 46 including utilizing a first portion of the sample to form said first count and utilizing a second portion of the sample to shift said at least one of the white blood cell populations or a subset thereof and form said second count.

51. The method as defined in claim 46 including said two electronic parameters being a low frequency and a high frequency signal.

52. A method for determining at least one not otherwise obtainable white blood cell population or population subset in a whole blood sample or portion thereof for identification and/or enumeration and/or study, comprising:

shifting at least one white blood cell population or subset population electronic sensing characteristic contribution with respect to other white blood cell populations or subset populations by binding microspheres having a monoclonal antibody bonded thereto specific to at least one of said white blood cell populations or subset thereof to at least one of said white blood cell populations or a subset thereof, said microspheres being substantially smaller than said cells; and electronically sensing and directly counting at least said shifted population with at least two different electronic parameters to obtain the contribution of said shifted population to said sample.

* * * * *